United States Patent [19]

Scanlon

[11] Patent Number: 5,618,702
[45] Date of Patent: Apr. 8, 1997

[54] PCR AMPLIFICATION OF MRNA

[75] Inventor: Kevin J. Scanlon, Pasadena, Calif.

[73] Assignee: City of Hope, Duarte, Calif.

[21] Appl. No.: 102,946

[22] Filed: Aug. 6, 1993

Related U.S. Application Data

[63] Continuation-in-part of Ser. No. 234,096, Aug. 19, 1988, which is a continuation-in-part of Ser. No. 46,127, May 5, 1897, abandoned.

[51] Int. Cl.$^6$ .................................................. G12P 19/34
[52] U.S. Cl. ................................................................ 435/91.2
[58] Field of Search ............................... 435/91.2, 77, 78

[56] References Cited

PUBLICATIONS

Soncho–Tello et al., Endocrinology 130 (3):1359–1364 (1992).
Watson et al., *Molecular Biology of the Gene* 4th Gdn: The Benjamin/Cummings Publishing Company, Inc., Menlo Park, CA, 1987, pp. 626–629.
Scanlon et al. J. Clin. Lab. Analysis 3(5):323–329 (1989).

*Primary Examiner*—Stephanie W. Zitomer
*Attorney, Agent, or Firm*—Rothwell, Figg, Ernst & Kurz

[57] ABSTRACT

A method for producing a contaminating DNA free PCR amplification product of mRNA is disclosed. The mRNA amplification product is of lower molecular weight and is readily separated, e.g., by gel electrophoresis, from any amplified cellular DNA contaminant.

7 Claims, 7 Drawing Sheets

SEQUENCE LISTING ( 1 ) GENERAL INFORMATION:

( i i i ) NUMBER OF SEQUENCES: 6

( 2 ) INFORMATION FOR SEQ ID NO: 1:

( i ) SEQUENCE CHARACTERISTICS:
      ( A ) LENGTH: 24
      ( B ) TYPE: Nucleic
      ( C ) STRANDEDNESS: Single
      ( D ) TOPOLOGY: Unknown ( x i ) SEQUENCE DESCRIPTION: SEQ ID NO: 1:

```
            TCCAGCTTGT  ACCTGCAGGA  TCTG                                    24
```

( 2 ) INFORMATION FOR SEQ ID NO: 2:

( i ) SEQUENCE CHARACTERISTICS:
       ( A ) LENGTH: 21
       ( B ) TYPE: Nucleic
       ( C ) STRANDEDNESS: Single
       ( D ) TOPOLOGY: Unknown ( x i ) SEQUENCE DESCRIPTION: SEQ ID NO: 2:

```
            AGGAGCCTGC  CTTTCCAGAG  A                                       21
```

( 2 ) INFORMATION FOR SEQ ID NO: 3:

( i ) SEQUENCE CHARACTERISTICS:
       ( A ) LENGTH: 24
       ( B ) TYPE: Nucleic
       ( C ) STRANDEDNESS: Single
       ( D ) TOPOLOGY: Unknown ( x i ) SEQUENCE DESCRIPTION: SEQ ID NO: 3:

```
            CGGTGTCTCC  TCATGGAGCA  CCAG                                    24
```

( 2 ) INFORMATION FOR SEQ ID NO: 4:

( i ) SEQUENCE CHARACTERISTICS:
       ( A ) LENGTH: 20
       ( B ) TYPE: Nucleic
       ( C ) STRANDEDNESS: Single
       ( D ) TOPOLOGY: Unknown ( x i ) SEQUENCE DESCRIPTION: SEQ ID NO: 4:

```
            TGAGGAGCGA  TGACGGAATA                                          20
```

( 2 ) INFORMATION FOR SEQ ID NO: 5:

( i ) SEQUENCE CHARACTERISTICS:
       ( A ) LENGTH: 20
       ( B ) TYPE: Nucleic
       ( C ) STRANDEDNESS: Single
       ( D ) TOPOLOGY: Unknown ( x i ) SEQUENCE DESCRIPTION: SEQ ID NO: 5:

```
            GACTTGGTGT  TGTTGATGGC                                          20
```

( 2 ) INFORMATION FOR SEQ ID NO: 6:

( i ) SEQUENCE CHARACTERISTICS:
       ( A ) LENGTH: 20
       ( B ) TYPE: Nucleic
       ( C ) STRANDEDNESS: Single
       ( D ) TOPOLOGY: Unknown ( x i ) SEQUENCE DESCRIPTION: SEQ ID NO: 6:

```
            ACCTCTATAG  TAGGGTCGTA                                          20
```

PCR AMPLIFICATION OF MRNA

RELATED APPLICATIONS

This application is a continuation-in-part of Ser. No. 234,096 filed Aug. 19, 1988 which is a continuation-in-part of application Ser. No. 046,127 filed May 5, 1987 and now abandoned.

FIELD OF THE INVENTION

It is known to anneal oppositely oriented primers to a RNA template followed by addition of reverse transcriptase to achieve first strand polymerization. PCR amplification is achieved by ensuing cycles of denaturation, annealing and polymerization mediated by a heat-stable DNA polymerase. Application of this technology to extend assays based on changes in gene expression to the messenger level is impeded by the presence in the gene transcripts of contaminant DNA transcription template sequences. A time consuming and inefficient approach to this problem involves pre-amplification removal of the DNA contaminant by DNase.

SUMMARY OF THE INVENTION

This invention provides a method for producing a DNA free PCR amplification product of mRNA from a cellular DNA contaminated gene transcript. The mRNA amplification product of the invention necessarily being of lower molecular weight is readily separated, e.g., by gel electrophoresis from any amplified cellular DNA contaminant.

DESCRIPTION OF THE FIGURES

FIG. 4A is identical with FIG. 2(a) in parent application Ser. No. 046,127 filed May 9, 1987, now abandoned.

FIG. 4B is identical with FIG. 2(a) of parent application Ser. No. 234,096 filed Aug. 19, 1988.

In FIG. 4A, primer sequences #1 (bases 925–947) and #3 (bases minus 3–21) are indicated. These primer sequences are complementary to exons in the DTMP synthase gene. This primers #1 and #3 flank an intron at bases 194 to 216.

DETAILED DESCRIPTION OF THE INVENTION

Gene transcript mRNA is frequently contaminated with sequences from the DNA transcription template. PCR amplification of such contaminated gene transcripts yields correspondingly a contaminated DNA amplification product of little utility. Heretofore this problem has been inefficiently addressed by the addition of DNase to remove the DNA contaminant from the reverse transcriptase free gene transcript. See, e.g., Example 4 at page 15, lines 4 to 25 of parent application Ser. No. 234,096.

This invention provides a substantially template DNA free direct PCR amplification product of mRNA present in the transcript of a gene having an intron flanked by two exons.

The mRNA in the transcript of a gene having an intron flanked by two exons has one sequence complementary to only one of the intron flanking exons and an abutting sequence complementary only to the other intron flanking exon.

Pursuant to this invention, oppositely oriented primers complementary to each of the abutting mRNA sequences and to the corresponding exon sequence from which the mRNA was transcribed are selected and annealed to the mRNA and DNA components of a gene transcript.

Addition of reverse transcriptase yields first strand polymerization. PCR amplification in normal manner by cycles of denaturation, annealing and polymerization in the presence of heat stable DNA polymerase yields a mixed DNA amplification product. One strand of one component of this DNA product has the target mRNA sequence. The other DNA component is amplified mRNA transcription template.

The amplified component having the mRNA sequence strand which contains no intron sequences is of substantially lower molecular weight than the amplified transcription template DNA which contains such intron sequences. This molecular weight difference is utilized, e.g., by conventional gel electrophoresis to separate the PCR product having the mRNA strand from the PCR amplification mixture. If desired, the separated product may be denatured in known manner to provide amplified mRNA substantially free of transcription template DNA contamination.

The primers useful in the invention are preferably about 15 to 25 bases in length. Twenty base primers facilitate efficient PCR amplification. In general, adequate product is provided by 20 to 30, preferably 25, rounds of amplification. Inclusion of ribonuclease A after completion of round one tends to eliminate RNA which may compete for primer binding in subsequent rounds.

The replicated mRNA sequence preferably contains a restriction site to facilitate identification in the reaction product by hybridization with a complementary probe.

The exemplified embodiments of the invention describe the production of substantially DNA free in mRNA from human c-myc and H-ras and TS transcripts.

EXAMPLE I

Figure 2A:
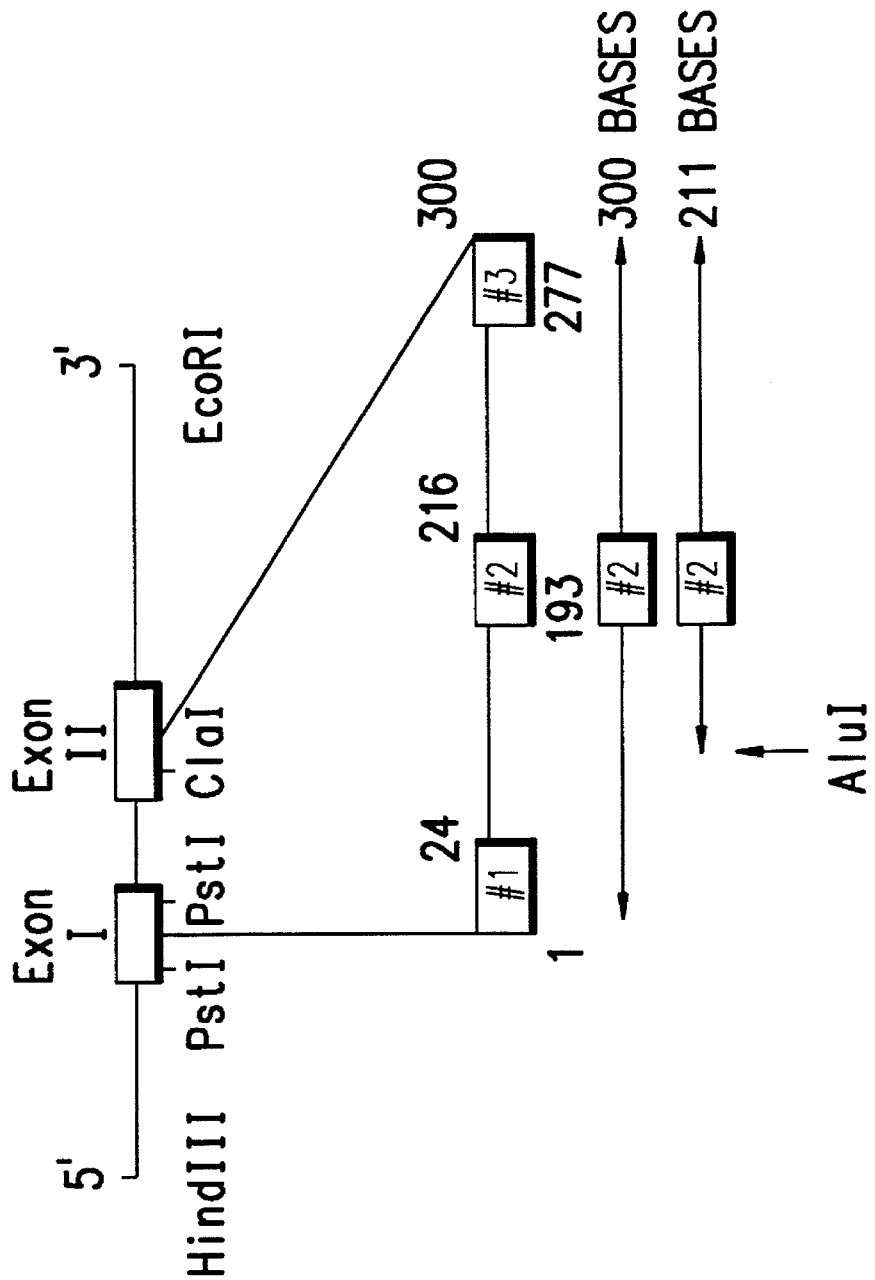
FIG. 2A is a schematic map which identifies the target and primer sequences and the position of the primers for the human c-myc oncogene.

The sequence of the human c-myc gene is set forth in *Proc. Natl. Acad. Sci.* 80:3642 (1983). As appears from that reference and as depicted by FIG. 2A, the human c-myc gene includes an intron including bases 1 to 300. An exon I including bases 1 to 24 flanks one terminus of the intron. An exon II including bases 277 to 300 flanks the other terminus of the intron.

Primers complementary to exon I and II sequences useful in the invention to the produce substantially DNA free amplification product of c-myc mRNA are also depicted by FIG. 2A. Specifically, 5'-3' primer c-myc #I is complementary to exon 1, bases 1–24 having a sequence of TCC AGC TTG TAC CTG CAG GAT CTG (SEQ ID NO: 1). 5'-3' primer c-myc #II, complementary to exon 2, bases 279–300 has a sequence 3' AGG AGC CTG CCT TTC CAG AGA 5' (SEQ ID NO: 2).

c-myc #3, bases 193–216 has a sequence 5'-CGGTGTCTCCTCATGGAGCACCAG-3' (SEQ ID NO: 3) may be used as the probe to detect the amplified sequence. This 300 base sequence contains a cleavage site for Alu I at position 88 which yields two fragments of 211 and 89 base pairs in length upon digestion. Note that only one of the cleavage fragments (the 211 base pair one) contains the sequence complementary to c-myc #2, so that hybridization of the digested PCR product with the end labeled probe should yield only one band.

Figure 1:
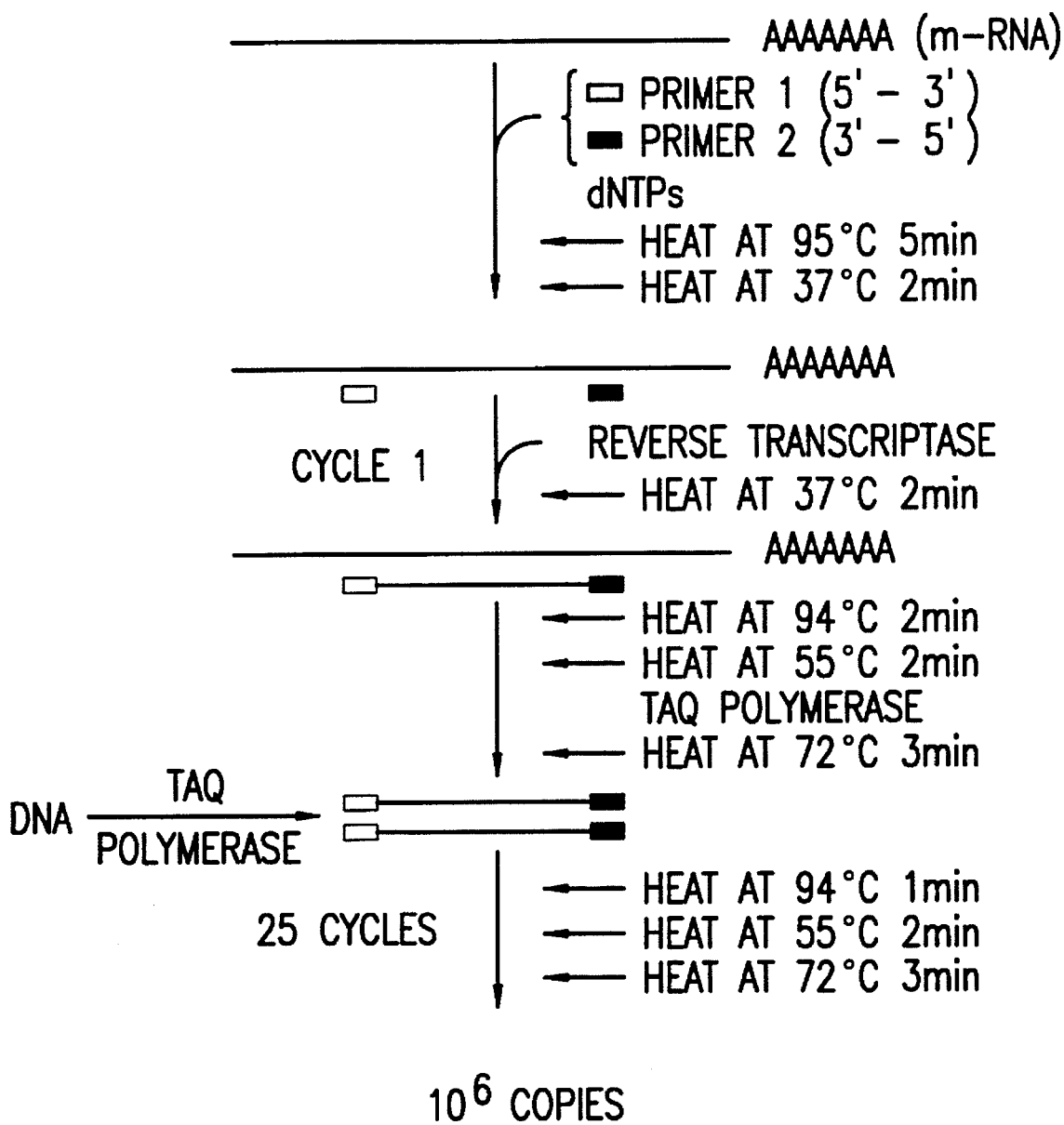
FIG. 1 is a generalized schematic diagram outlining some of the steps of one embodiment of the invention.

As shown generally by FIGS. 1 and 2A, primers c-myc I and c-myc II which span an intron are annealed to a c-myc gene transcript isolated directly from human cells. Thus, if there is DNA in the RNA sample, it will yield a product of more than 300 bases.

First strand polymerization is achieved by the addition of reverse transcriptase. PCR amplification by about twenty five cycles of denaturation, annealing and polymerization mediated by heat stable Taq DNA polymerase yields an amplification product mixture containing first and second double stranded DNA components. The first double stranded DNA component consists only of the 300 base target mRNA sequence and its complement. The second double stranded DNA component of the PCR amplification product consists of mRNA transcription template DNA having more than 300 bases and its complement.

The second amplification product component is of greater molecular weight because it includes intron sequence of the DNA transcription template which are not present in the first amplification product component.

The PCR amplification product mixture is separated by electrophoresis on 1.8% agarose gel. The DNA corresponding to the RNA component of the amplification product mixture is quantitated accurately with minimal loss by alkaline blotting to nylon filters (Zeta probe) to covalently bind the DNA to the membrane.

Figure 2B:
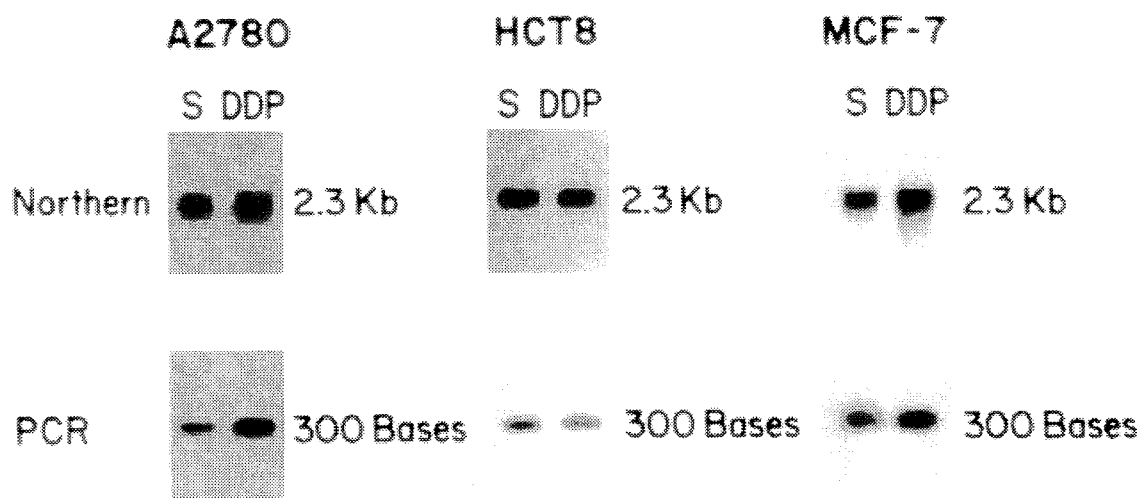
FIG. 2B depicts an analysis of c-myc expression in three cis-platin sensitive (S) and resistant (DDP) cell lines as determined by PCR and Northern assay.

As shown by the FIG. 2B analysis of c-myc expression in cis-platin sensitive (S) and resistant A2780, HCT8 and MCF-7 cells the PCR and conventional Northern assays yield a like result. The PCR assay contained only 2 ng of RNA per assay and gave a signal at 300 bases and the Northern analysis of 2 µg of RNA per lane gave a 2.3 Kb signal.

This experiment is depicted by FIG. 5 of Scanlon, et al., *Anticancer Research* 9:1301–1312 (1989).

EXAMPLE II

The complete nucleotide sequences of the human H-ras oncogene are set forth in *Science* 220:1061 (1983).

As the cited reference shows and as depicted by FIG. 3, the H-ras gene includes exons I, II, III and IV. A first intron is flanked by exons I and II, a second intron is flanked by exons II and III, and a third intron is flanked by exons III and IV. Transcription of this DNA template yields mRNA free of any sequences complementary to any of the three intron sequences.

This example and FIG. 3 illustrate the amplification of a target mRNA having abutting sequences complementary to exon I and exon II of H-ras cDNA as described in Scanlon, et al., *J. Chem. Lab Anal.* 3:323–329 (1989).

Specifically, the H-ras gene transcripts were isolated from a normal colon (N) tissue sample, two colon carcinoma patients who failed treatment with cis-platin/5-FUra (PK), and cisplatin/ara-C (HG) and the human colon carcinoma cell line HCT8 sensitive (S) and 3-fold resistant (DDP) to cisplatin. The primers were synthesized for the H-ras gene and the mRNA samples were subjected to the PCR assay or to Northern blotting for purposes of comparison. The results, depicted in FIGS. 3A and 3B, demonstrate elevated expression of the H-ras gene in tumor cells over normal cells.

Figure 3A:
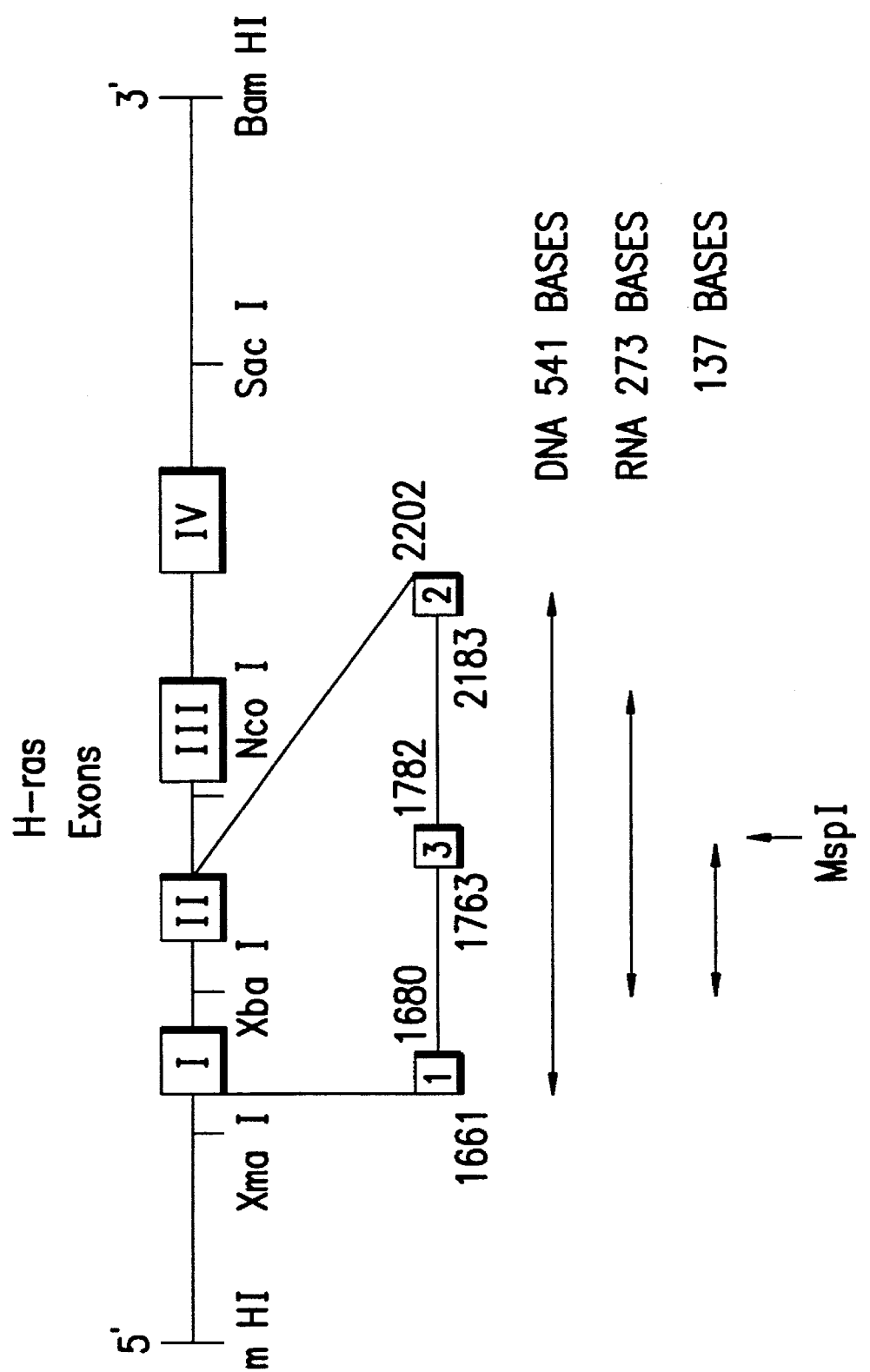
FIG. 3A is a schematic map which identifies the target and primer sequences and the position of the primers for the human H-ras oncogene.
Figure 3B:
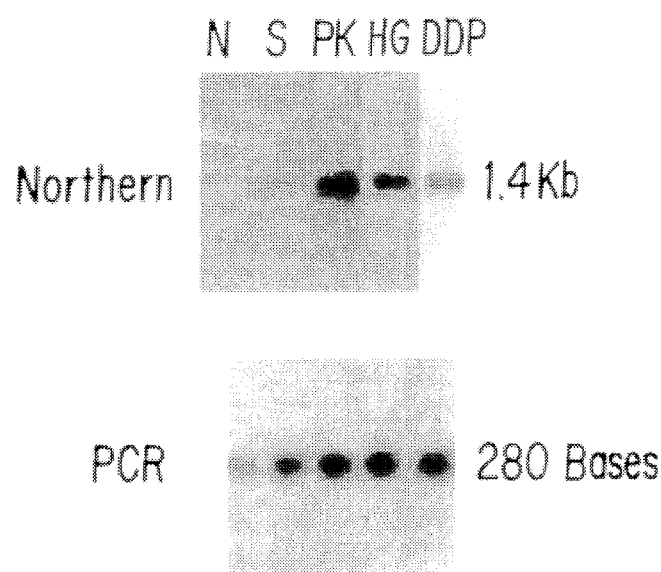
FIG. 3B depicts a comparison of the expression of H-ras as determined by PCR and Northern assay. The Figure depicts results based upon isolated mRNA from a normal colon (N) tissue sample, two colon carcinoma patients who failed treatment with cis-platin/5-FUra (PK) and cisplatin/ara-C (HG) and the human colon carcinoma cell line HCT8 sensitive (S) and 3-fold resistant (DDP) to cisplatin.
Figure 4A:
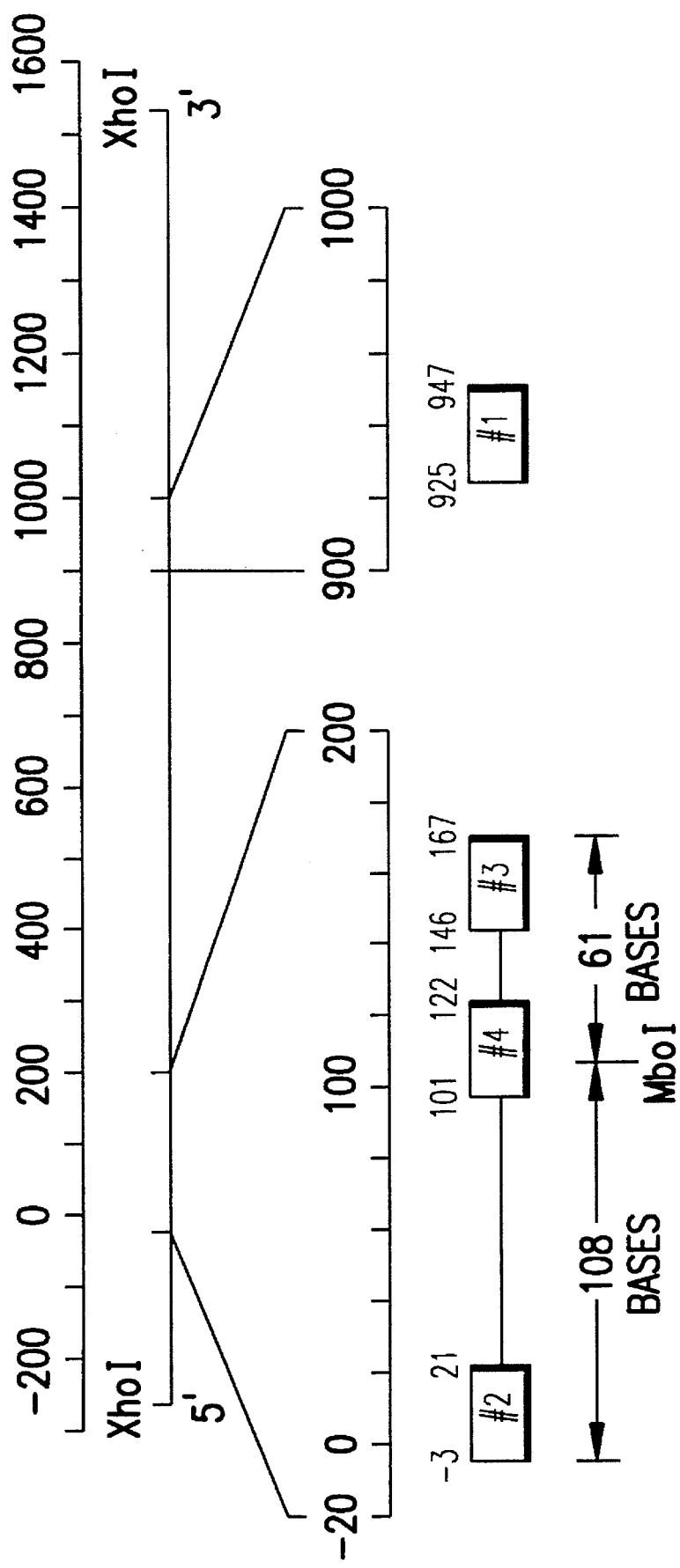
FIG. 4A is a schematic map which identifies the target mRNA and the primer sequences #1, #2 and #3 and the position of the primers for the human thymidylate synthase (TS) gene.
Figure 4B:
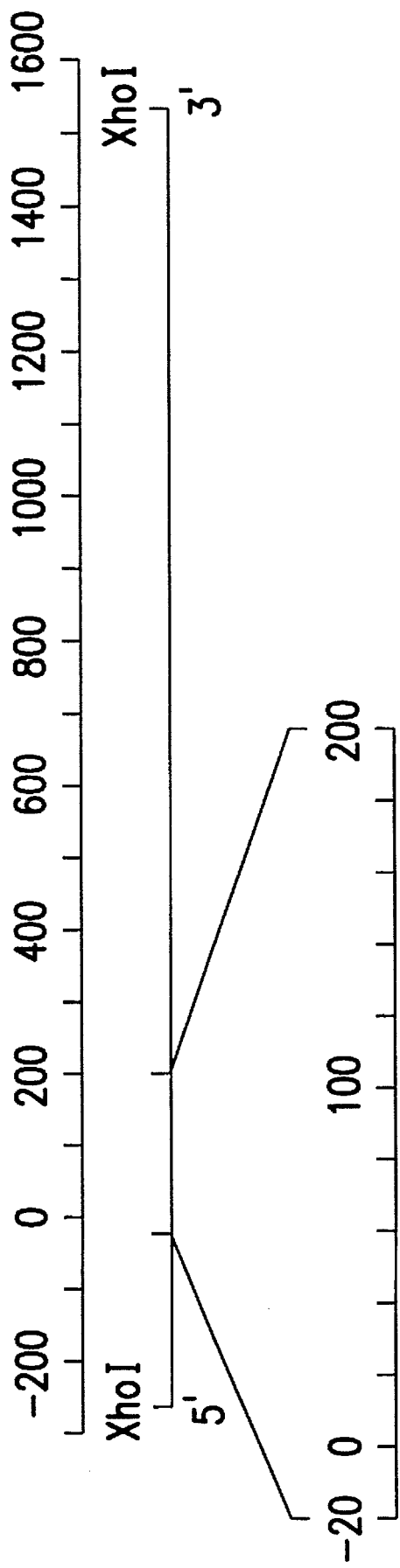
FIG. 4B is a schematic map which identifies the target mRNA and primer sequences and the position of the primers for the human TS gene.
Figure 4B:
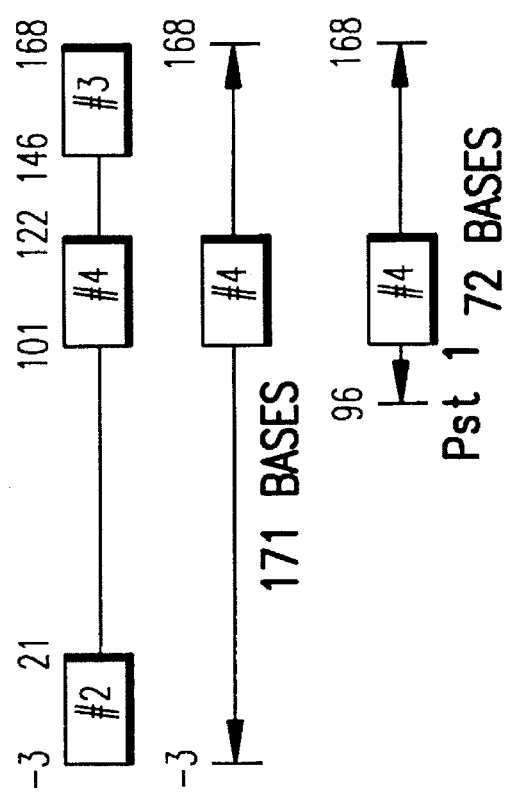

Referring to FIGS. 3A and 3B, the amplified fragment stretches from 1661 to 2202. H-ras #1 is a sense oligonucleotide, spans nucleotides 1661–1680, and contains the sequence: 5'-TGAGGAGCGATGACGGAATA-3' (SEQ ID NO: 4). H-ras #2 is an antisense oligonucleotide, encodes nucleotides 2183 to 2202 and is represented by the following sequence: 5'-GACTTGGTGTTGTTGATGGC-3' (SEQ ID NO: 5). H-ras #3 is the antisense oligonucleotide spanning 1763–1782 and encodes the sequence: 5'-ACCTCTATAGTAGGGTCGTA-3' (SEQ ID NO: 6). H-ras #1 and H-ras #2 are used as primers for the polymerization assay and H-ras #3 was used as the probe to detect the amplified sequence. The 273-base amplification target sequence contains a cleavage site for MspI at position 1786, which yields two fragments of 136 and 137 base pairs in length upon digestion. Only the 137 base pair cleavage fragment contains the sequence complementary to H-ras #3, so that hybridization of the digested PCR product with the end labeled probe should yield only one band.

I claim:

1. A method for producing a substantially contaminating DNA free PCR amplification product of a mRNA from a cellular DNA contaminated gene transcript, the method comprising:

(a) providing a gene transcript mRNA,
   said gene having an intron flanked by first and second exons,
   said gene transcript mRNA being contaminated with template DNA from which said mRNA was transcribed,
   said mRNA having a first portion complementary only to a sequence of said first exon and an abutting second portion complementary only to a sequence of said second exon;

(b) providing first and second PCR primers, said first PCR primer being complementary to said first portion of said mRNA and, said second PCR primer being complementary to the completment of said abutting second portion of said mRNA;

(c) annealing said primers to said mRNA and thereafter, (d) reacting said mRNA having said primers anealed thereto with reverse transcriptase to provide double stranded DNA, one strand of which has the sequence of said mRNA and the other strand of which is complementary to said sequence of said mRNA;

(e) reacting said double stranded DNA with said first and second primers in a PCR to simultaneously amplify (i) said double stranded DNA and (ii) said DNA contaminant to provide an amplification reaction product containing amplified double stranded DNA which has no sequence complementary to said intron and amplified DNA contaminant which includes said intron, wherein said amplified double stranded DNA which has no sequence complementary to said intron is of substantially lower molecular weight than said amplified DNA contaminant which includes said intron; and (f) utilizing the difference in molecular weights to separate said amplified double stranded DNA from said amplified DNA contaminant to produce a substantially contaminating DNA free PCR amplification product.

2. A method as defined by claim 1 in which said gene transcript is a transcript of a human oncogene.

3. A method as defined by claim 1 in which said gene transcript is a transcript of a human H-ras oncogene or a human c-myc oncogene or a human thymidylate synthase gene.

4. A method as defined by claim 1 in which said gene transcript is a transcript of a human c-myc gene.

5. A method as defined by claim 1 in which said transcript gene is a transcript of a human c-myc gene, said first primer has the sequence of SEQ ID NO: 1 and said second primer has the sequence of SEQ ID NO: 2.

6. A method as defined by claim 1 in which said gene transcript is a transcript of a human H-ras oncogene.

7. A method as defined by claim 1 in which said transcript gene is a transcript of a human H-ras gene, said first primer has the sequence of SEQ ID NO: 4 and said second primer has the sequence of SEQ ID NO: 5.

* * * * *